Figure 2:
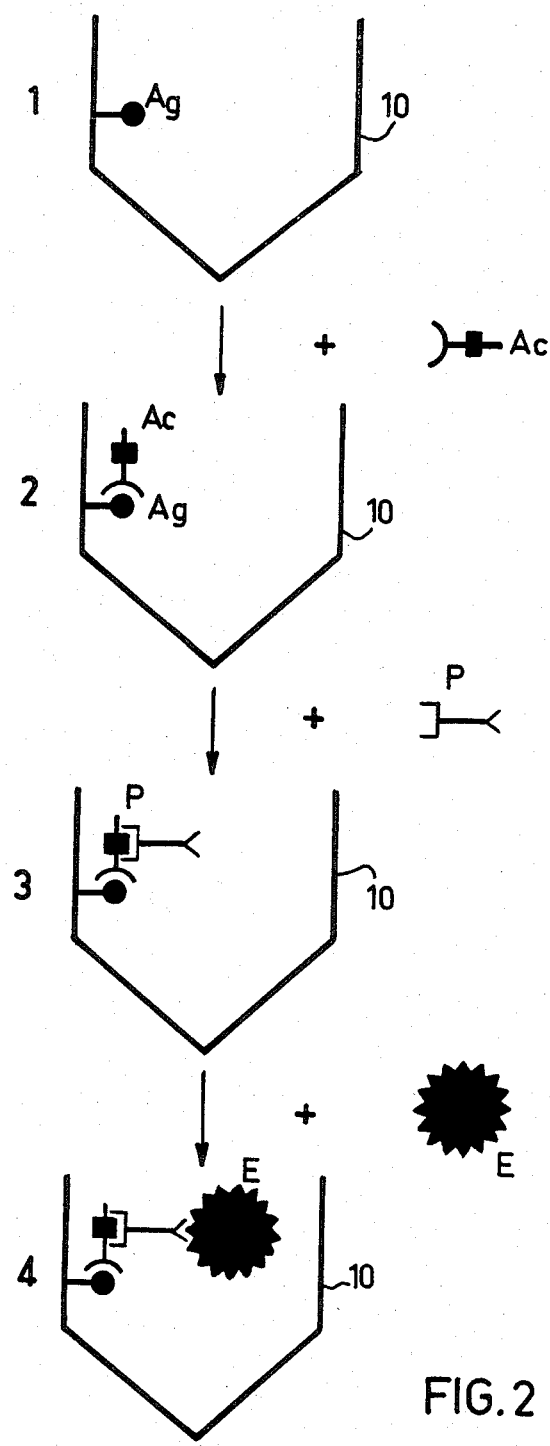

United States Patent [19]

Avrameas et al.

[11] Patent Number: 4,526,871
[45] Date of Patent: Jul. 2, 1985

[54] CONJUGATE OBTAINED BY COUPLING A LECTIN AND A SPECIFIC LIGAND, CONTAINING SUCH A CONJUGATE AND ITS APPLICATIONS IN BIOLOGY

[75] Inventors: Stratis Avrameas, La Celle Saint Cloud; Jean-Luc Guesdon, Paris, both of France

[73] Assignee: Institut Pasteur, Paris, France

[21] Appl. No.: 265,427

[22] Filed: May 20, 1981

[30] Foreign Application Priority Data

May 22, 1980 [FR] France ............................ 80 11470
Jul. 15, 1980 [CH] Switzerland ....................... 5428/80

[51] Int. Cl.³ .................... G01N 33/54; G01N 33/58; G01N 33/60
[52] U.S. Cl. .................................. 436/504; 436/542; 436/532; 436/800; 436/804; 436/827; 435/7
[58] Field of Search .................. 424/1, 12; 23/230 B; 435/7; 436/504, 542, 532, 800, 804, 827

[56] References Cited

U.S. PATENT DOCUMENTS 4,289,747  9/1981  Chu ............................ 424/1

FOREIGN PATENT DOCUMENTS 7537392   7/1977  France .
WO80/02296  10/1980  PCT Int'l Appl. .

OTHER PUBLICATIONS

Guesdon et al, J. Immunol. Methods, 39 (1980) 1–13.
Stratis Avrameas, "Coupling of Enzymes to Proteins with Glutaraldehyde", 1969, *Immunochemistry*, pp. 43–47.

Primary Examiner—Christine M. Nucker
Attorney, Agent, or Firm—Frost & Jacobs

[57] ABSTRACT

The present invention relates to a conjugate of a specific ligand and a lectin, by covalent bonding.

The product of the invention may, for example, be the conjugate of Concanavalin A and an antigen, a hapten, an antibody, a hormone or its receptor, an enzyme or its inhibitor or a lectin. Coupling being effected by means of glutaraldehyde or p-benzoquinone.

8 Claims, 2 Drawing Figures

DIAGRAM A

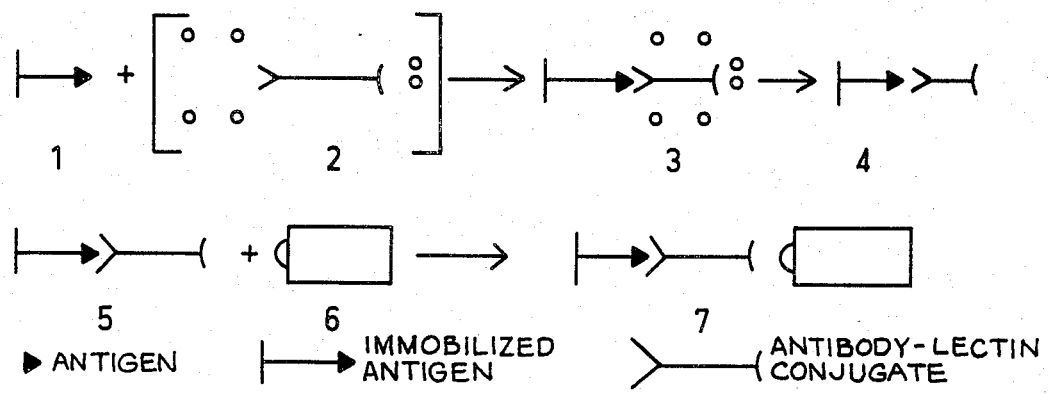

● ANTIGEN
⊢→ IMMOBILIZED ANTIGEN
>─( ANTIBODY-LECTIN CONJUGATE

○ LOW MOLECULAR WEIGHT SUGAR SPECIFIC TO THE LECTIN.

⊲▭ LABELLING SUBSTANCE ABLE TO REACT WITH LECTIN.

DIAGRAM B

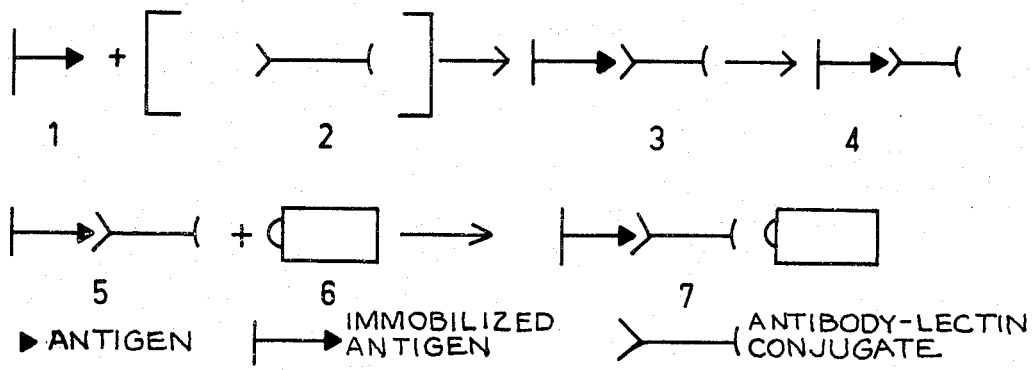

● ANTIGEN
⊢→ IMMOBILIZED ANTIGEN
>─( ANTIBODY-LECTIN CONJUGATE

⊲▭ LABELLING SUBSTANCE ABLE TO REACT WITH LECTIN.

DIAGRAM C

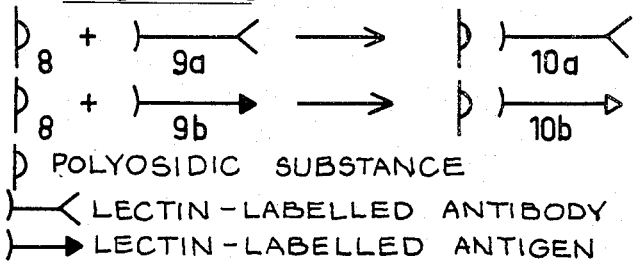

▷ POLYOSIDIC SUBSTANCE
)─< LECTIN-LABELLED ANTIBODY
)─→ LECTIN-LABELLED ANTIGEN

FIG.1

CONJUGATE OBTAINED BY COUPLING A LECTIN AND A SPECIFIC LIGAND, CONTAINING SUCH A CONJUGATE AND ITS APPLICATIONS IN BIOLOGY

The present invention relates to a conjugate obtained by coupling a lectin and a specific ligand, to a process for obtaining same and to its applications in biological techniques, notably for the localization, identification and assaying or determination of antibodies or antigens. The conjugate of the invention is particularly suited for use as an universal reagent in various types of biological assays, notably immunological assays.

In immunology, notably, use has already been made of conjugates of antibodies or antigens with various substances as labellers such as, for example, enzymes, radioisotopes, ferritine, red blood cells and fluorochromes. Such conjugates are used as reagents in various immunological processes for the localization, the identification or the determination of humoral or cellular components.

For more details of these known conjugates, reference may be made to the following publication: "Handbook of experimental immunology", 3 vol., Ed. D. M. Weir (1978) Blackwell Scientific.

A new series of conjugates has now been found which can have a wide range of applications; these are conjugates of a lectin and of a specific ligand.

The present invention, therefore, relates to a novel product consisting of conjugates of a lectin and of a specific ligand.

Although the following detailed information relates to certain particular lectins, it should be noted that the teachings of the present specification are valid for all lectins.

Lectins are proteins of various origins and, among other things, those obtained from plants, which react in a specific manner and by non-covalent bonds with certain glycosidic residues.

As examples of lectins may be mentioned: Concanavalin A extracted from *Canavalia-ensiformis;* the lectin extracted from *Ricinus communis,* the lectin extracted from *Triticum vulgare* i.e. the wheat germ agglutinin (WGA). A detailed description of lectins will be found in the following books which are cited as references in the present specification:
—Science, 1972, vol. 177, p. 949–959,
—Annales d'Immunologie, 1979 vol. 1c No. 1, p.4–16.

It will be noted that Concanavalin A reacts specifically with methyl-α-D-mannoside; lectin extracted from Ricinus communis reacts with D-galactose, and the lectin extracted from *Triticum vulgare* reacts specifically with N-acetyl-glucosamine.

Among the lectins, Concanavalin A possesses the widest range of specificity; it can be isolated easily and in large amounts. It is therefore easy and cheap to use it. The WGA lectin gives also excellent results. According to the invention any lectin may be used; the choice of lectin depends on its availability and also on its specificity.

In the present specification, "specific ligand" means any soluble substance that can react specifically with another biological or particulate substance. "Soluble substance" means any substance soluble in the media usually used for biological reactions, and can be aqueous media, such as physiological media, or mixtures of aqueous and organic media.

Furthermore, the specific ligand used according to the invention should be such that the lectin-ligand conjugate of the invention is soluble in an aqueous medium, whether or not in the presence of the specific sugar of the lectin used, according to the application in which the said conjugate is used.

"Aqueous medium" according to the invention designates aqueous media, whether buffered or not, usually used in biology, such as phosphate buffer solutions; buffer solutions containing a detergent such as "Tween", or gelatine, bovine serum albumin, bovine lactalbumin and other substances usually used in such fields.

The specific ligands that comply with such a definition are, notably, antibodies, macromolecular antigens or haptens, hormones and their receptors, enzymes and their inhibitors, lectins and similar substances. Among the specific ligands mentioned hereinabove, antibodies and antigens are the most usually used.

The product of the invention is obtained by coupling a lectin with the ligand by means of a suitable coupling agent such as, for example, glutaraldehyde and benzoquinone. Coupling is advantageously effected by covalent bonds.

Lectin-specific ligand coupling is effected by a process similar to those used for protein coupling.

For example, lectin-specific ligand coupling can be carried out by a process similar to that described for obtaining antibody-enzyme conjugates in Scand. J. Immunol., vol. 8 suppl. 7 p.7–23,1978. Such a coupling process consists in contacting in one or more steps, a coupling agent with the substance to be coupled.

When benzoquinone is used as the coupling agent, it is of no consequence whether the lectin or the specific ligand is activated first. As a reference illustrating the coupling method with benzoquinone, French Pat. No. 75 37 392 (publication No. 2.334.107)may also be mentioned.

When using glutaraldehyde as the coupling agent, the lectin and the ligand are advantageously mixed and the glutaraldehyde is added to said mixture in amounts suited to effect coupling. However, this coupling can also be effected in two steps: contacting one of the reagents with glutaraldehyde, removing the excess glutaraldehyde and adding the other reagent. This coupling is substantially carried out according to the process disclosed in an article of S. AVRAMEAS [Immunochemistry vol.6 1969].

In many cases, glutaraldehyde is suited for use as a coupling agent, for example, with antigens or antibodies. The following table illustrates the preparation of antibody-lectin conjugates using glutaraldehyde as coupling agent. However, these examples are not exhaustive.

TABLE 1

| Lectin | | Amount of antibody* | Volume of glutaraldehyde (1%) |
|---|---|---|---|
| Origin | Quantity | | |
| Lens culinaris | 1.5 mg | 0.7 mg | 20 μl |
| Triticum vulgare | 0.7 mg | 0.4 mg | 20 μl |
| Ricinus communis | 1.7 mg | 0.9 mg | 20 μl |
| Canavalia ensiformis | 4 mg | 2 mg | 20 μl |

*The antibody used was sheep anti-rabbit immunoglobulin antibodies.

The lectin and the antibody are dissolved in a 0.1M phosphate buffer pH 6.8;20 μl of 1% glutaraldehyde is added to this mixture. The total volume of the reaction mixture amounts to 1 ml.

But, when the lectin does not possess primary amine groups, glutaraldehyde cannot be used for coupling. In this case, other coupling agents may be used. These should enable lectin to be coupled to another ligand without substantial loss of activity of one and/or the other component.

Thus, with succinyl-concanavalin A, which no longer possesses primary amine groups, glutaraldehyde cannot be used, but it is possible to obtain an effective antibody succinyl-concanavalin A conjugate with p-benzoquinone.

The lectin-specific ligand conjugate of the invention may be characterized by its ability to react with a specific substance and, concomitantly, with a specific labeller for lectin. For example, if the lectin-ligand conjugate is a lectin-antigen product, it might be characterized by its capacity to react with the corresponding specific substance viz, the corresponding antibody, and by its ability to react with a specific labeller for lectin, such as a glycoproteinic enzyme.

It may be advantageously stored as an aqueous solution at low temperature, for example, at 4° C.

It can also be mixed with glycerol(generally 50/50) and stored thus at 4° C., or in a freezer at −20° C.

The lectin-specific ligand conjugate of the invention is suited for use as a reagent in various immunological processes for the localization, identification and assaying or determination of biological substances, such as in immunological assays of the non-competitive, the double antibody or the competitive types. It is advantageously used in the form of an aqueous solution, whether or not this is buffered, which may contain an excess of a low molecular weight sugar, specific to the lectin of the product of the invention.

It should be noted that it was previously proposed to use lectin for the detection of cancers by determination of galactosyl-transferase activity in the cells. In this respect, reference may be made to patent application WO No. 80/02 296 which concerns an improved process for detection of cancers by determination of galactosyl-transferase in the cells by means of a labeller specific to this activity. The labeller used in this process should have a specific activity for galactose or galactose residues. An example of an appropriate labeller useful for this process is constituted by a lectin coupled with a dye, for example a fluorescent dye. In this process, it is the lectin which interferes in the determination of the searched activity. On the contrary, in the immunological processes hereinabove cited, in which the invention product may be used, it is the specific ligand which reacts with the substance to be assayed and not the lectin as in the process of patent application WO No. 80/02 296.

The lectin-ligand conjugate of the invention, in the form of an aqueous solution containing an excess of a low molecular weight sugar, specific to the lectin, is particularly well suited for use as a reagent in immunological techniques, wherein one of the reagents, or the substance to be identified is insoluble or is immobilized on an insoluble substrate. It is, therefore, particularly suited to types of assays where an insoluble substrate is used. But the product of the invention can also be used in the soluble phase.

As an illustrative example, the appended FIG. 1 shows the diagram of a process for the identification of an immobilized antigen (diagram A).

In order to identify the immobilized antigen (1), the lectin-ligand conjugate (2), dissolved in an an aqueous medium containing a low molecular weight sugar specific to the lectin of the conjugate, is, according to the invention, added, the ligand being an antibody in this particular case.

The antibody portion of the conjugate (2) reacts with the immobilized antigen whereas, owing to the presence of excess sugar, the lectin portion of said conjugate cannot react with other glycosidic substances which might be present in the reaction mixture.

The following step of this process consists in washing the antigen-conjugate complex (3) to remove the sugar and the excess conjugate (2). A labeller bearing a polyosidic portion able to react with lectin is then added. The labeller is thereafter identified by any suitable means, optionally after washing.

According to an another embodiment, the antigen can also be identified according to reaction diagram B shown in the appended FIG. 1. In this case, the lectin-ligand conjugate is used in solution in the absence of the specific sugar of the lectin. It should, however, be noted that this reaction diagram can only be used when the antigen to be identified is not a substance comprising glycosidic groups capable of reacting with lectin.

In the above process for the identification of an antigen, the lectin coupled to the antibody acts as a labeller acceptor. Because a large number of labellers have polysaccharide portions, or because saccharide residues can easily be bound to them, the same antibody-lectin or lectin-antigen conjugate can be used in combination with a large number of labellers. According to the invention, "labeller" designates all substances, of any nature enabling an identification or a determination to be effected. As examples of labellers the following may be mentioned: enzymes, fluorescent derivatives, radioactive elements, red blood cells and similar products.

Some enzymes which can be used as labellers are not glycoproteins; however, in order for them to be used with a conjugate according to the invention in immunoenzymatic assays, it is possible to couple or bind glycosidic fractions to these enzymes. One means for binding such fractions consists in chemically grafting a glycidic copula onto the enzyme. Another means consists in coupling a holo-protein enzyme, (β-galactosidase for example) with a glycoprotein (such as peroxidase or glucose oxidase). For example, a glucose-oxidase-β-galactosidase may be prepared by mixing 2.5 mg (230 μl) glucose oxidase, 4.1 mg (410 μl)β-galactosidase and 50 μl 1% glutaraldehyde. Therefore, any labeller can be used insofar as it possesses glycosidic fractions or can be coupled or bound to such fractions.

The labeller can also be a substance comprising a fluorochrome, or a radioactive isotope or a particulate substance capable of reacting with a lectin.

An immunological technique which is respectively the immunoenzymatic technique (immunoenzymatic assay or histochemical detection), immunofluorescence (immunofluorimetric assay or histochemical detection), the radioimmunological technique, hemagglutination and other similar techniques corresponds to each of the above labellers.

As a non-limiting example, an assaying process using a lectin-ligand conjugate according to the invention will be described below.

This assaying process for the determination of a given biological substance comprises:

(1) immobilizing a substance having a binding affinity with respect to the biological substance to be assayed;

(2) incubating this substance with the medium containing the biological substance to be assayed;

(3) after washing, incubating the resulting reaction medium with a lectin-specific ligand conjugate in solution in an aqueous medium containing an excess of a sugar specific to the lectin, said ligand being capable of reacting specifically with said substance having an affinity for the biological substance to be assayed or with said biological substance itself;

(4) washing the resulting reaction medium and in incubating it with a labeller bearing glycosidic fractions capable of reacting with lectin;

(5) revealing the labeller by suitable means.

This process is suitable for the assay of antigens, antibodies, immunoglobulins and other substances of biological interest.

The substance having a binding affinity with respect to the biological substance to be determined can be any substance capable of binding to the said biological substance in a specific manner. For example, if the biological substance to be assayed is an antibody, the substance having binding affinity will be an antigen, and vice-versa.

According to this process, any labeller can be used such as those mentioned hereinabove, notably enzymes and red blood cells in which case step (5) is an enzymatic or erythroadsorption determination step.

The lectin-ligand conjugate of the invention has a particularly interesting application in immunological techniques using red blood cells as labellers. In known hemagglutination techniques it is necessary to use red blood cells sensitized by an antigen, for example. The conjugate of the invention makes it possible to avoid such sensitization because red blood cells are used as labellers to reveal the presence of the lectin-specific ligand conjugate, by means of the lectin. The assaying process according to the invention involving the use of red blood cells can be designated as specific erythroadsorption. Furthermore, by using this erythroadsorption procedure, a substantially smaller amount of red blood cells are used compared with conventional hemagglutination processes.

The media containing the biological substance to be assayed are generally sera. Due to the fact that sera present, from one species to the other, crossed reactions and they often contain anti-red blood cell antibodies, for example sheep anti-red blood cell antibodies, it should be necessary to take care to "absorb" with red blood cells the serum to be tested in order to avoid the wrongly positive reactions in the case wherein the erythroadsorption is used. Although such a technique uses means known by the one skilled in the art, certain embodiments will be indicated hereinafter.

In the case wherein the antibody or antigen to be assayed is not thermolabile this absorption will be effected in submitting the serum to the following steps, which consist of:

(a) decomplementing of the serum, i.e. in heating it at about 56° C. for about 30 min;

(b) adding to said serum an excess of sheep red blood cells, for example in order to obtain a concentration of red blood cells of 10%;

(c) leaving the serum to the ambient temperature for about 1 hour under an easy stirring;

(d) centrifugating in order to recover the purified serum and to remove the erythrocyte bottom.

In the case wherein the antibody or antigen to be assayed is thermolabile, the serum will not be decomplemented but it will be absorbed by red blood cells, for example sheep red blood cells, treated by a tanning agent, preferably by glutaraldehyde.

The serum so treated may be thereafter submitted to the assay process of the invention, step 5 thereof consisting in a determination by erythroadsorption.

The determination of the erythroadsorption may be carried out in several manners. For example, it may be visually verified that the red blood cells are adsorbed on the surface of the substrate on which the substance having a binding affinity for the biological substance to be assayed, was immobilized. In this case, the process allows the identification, in a given biological liquid, of a particular biological substance. If, on the contrary, the biological liquid does not contain the particular biological substance the erythrocytes will not be adsorbed and will form a layer in the bottom of the container, for example the wells of the microplates. The process of the invention also allows the quantitative determination of a given biological substance. In this respect, the erythrocytes which have not reacted are removed, for example by aspiration with a pipette. Thereafter, the adsorbed erythrocytes are lysed, for example with distilled water, and the substances released by the erythrocytes are assayed, for example haemoglobin or the substances artificially introduced by the experimenter by spectrophotometry preferably at 414 nm or at a near wavelength, which makes it possible to automate entirely the assaying process.

The haemoglobin may also be assayed by an enzymatic reaction. For example, peroxidase substrates may be used, such as ortho-dianisidine, or ortho-phenylenediamine. The reading is also effected by spectrophotometry at 400 nm for ortho-dianisidine and at 492 nm for ortho-phenylene-diamine.

The amount of substances released by red blood cells, for example, the amount of haemoglobin quantity, is proportional to the amount of the substance to be assayed, which allows, for example, the assay of an antigen or an antibody present in a sample by reference to a standard range of hemolysis of erythrocytes established under the same conditions.

The assay process of the invention by erythroadsorption is particularly appropriate for the assay of antibodies and antigens and it will be disclosed in more details hereinafter, without limiting the scope of the invention thereto, by reference to FIG. 2 on which the reaction diagram of this embodiment is represented.

In this FIG. 2, (1) represents the first step of the invention process in which antigens (Ag) are immobilized on the substrate (10). In this particular case of this figure, the substrate (10) represents a well in the form of a V of a microplate. The immobilization of the antigens, which are in the present case the substance having an affinity for the biological substance to be assayed, i.e. the antibody, is effected, for example by passive adsorption or, if necessary, by covalent binding according to the nature of the substrate.

The step (2) consists in an incubation of the immobilized antigen with the biological liquid containing the antibody (Ac) to be assayed, for example the serum to be tested. After this incubation step, wherein the antigen (Ag) interacts with the corresponding antibody (Ac), if it is present in the serum to be tested, the substrate is washed by means of a buffer-solution, for example a phosphate buffer solution, optionally containing a surfactant, such as "Tween", said solution will be hereinafter named PBS or PBS-Tween.

The step (3) of the invention process consists in incubating the substrate resulting from step (2) with a lectin-specific ligand conjugate (P) able to react with erythrocytes (E). In this particular case, the specific ligand is an antibody trained against the immunoglobulins of the human or animal species of the serum to be tested. After this incubation the resulting system is washed, as hereinabove disclosed, in order to remove the conjugate which has not reacted. Thereafter, erythrocytes are added, which are adsorbed by the conjugate only if the serum to be tested contains the antibody corresponding to the immobilized antigen; otherwise the erythrocytes are not adsorbed and fall down in the bottom of the container.

The quantitative assay, i.e. the determination of the amount of antibodies contained in the serum, will be easily carried out, as hereinabove disclosed, i.e. by lysis of the erythrocytes and determination of the amount of the substance released by erythrocytes, for example the amount of haemoglobin.

The use of hemolysing lectins for the obtention of the conjugate of the invention, may delete this last step of lysis of erythrocytes.

In FIG. 2, the reaction diagram of the assay process of the invention using erythrocytes as labeller (i.e. the process by erythroadsorption) was represented. The invention process using another labeller different from erythrocytes may be represented by the same reaction diagram except that another labeller is added instead of erythrocytes.

Any insoluble substrate presented in a definite form can be used as a substrate, such as a plate or a leaf, on in a particulate form. The substance from which said substrates are made may be chosen from among the following: cellulose or its derivatives, polyacrylamide, alkyl polymethacrylates and other polymers of natural or synthetic origin, and glass. However, it would be noted that in the preferred embodiment of the invention process by erythroadsorption, a substrate having the form of a container will be used.

Advantageously, microplates are used to immobilize the antigen or the antibody used in the above process; for example, polystyrene microplates. It was noted that microplates having cavities in V or U form are the more appropriate for the assay process by erythroadsorption.

For carrying out the process of the invention using a labeller different from erythrocytes, substrates in the form of gels may be also used, preferably magnetic gels, such as those described in French Pat. No. 75 36 889 (published under the No. 2.334.106) and French patent application No. 79 21 343.

It will be noted that the conjugate of the invention, used in the form of a solution, provides considerable advantages in the field of immunological determinations because its use does not make it necessary to effect separation, centrifugation or filtration steps, other than those imposed by the immobilization substrate of one of the reagents (for example, washing the substrate or separation by means of a magnet in the case of magnetic gels).

The assaying process defined hereinabove has exactly the same sensitivity as conventional immunoenzymatic assays, that is to say, in the order of 1 ng for antigens and of 10 to 20 ng for antibodies. This sensitivity is also approximately equal to that obtained with quantitative radioimmunology.

The lectin-specific ligand conjugate of the invention is also suited to binding antigens (9b) or antibodies (9a) to polyosidic substances or to those bearing oxide groups (8) to form the complex (10a or 10b), the bond being effected by means of the lectin as shown in diagram C on the appended FIG. 1.

The resulting complexes can be used in all processes where an insoluble phase is necessary, as in affinity chromatography, or with a view to the extraction of the characterization and/or the assay of an antigen or an antibody.

The invention will be now described by the following non-limiting examples in which the lectin used is Concanavalin-A (Con A).

EXAMPLE 1

Preparation of the lectin-antibody conjugate by means of glutaraldehyde

Pure sheep anti-rabbit Ig antibodies isolated by affinity chromatography were used.

The antibodies and the Con.A were dialyzed against 0.1M phosphate buffer pH 6.8 for 1 night at 4° C. The dialyzed antibodies (2 mg) and Con.A (4 mg) were mixed in a solution containing methyl-α-D-mannoside (0.1M). The total volume being 1 ml. 25 µl of an aqueous solution of glutaraldehyde was added to the mixture, which was then incubated for 3 hours at ambient temperature. Then, 50 µl of 2M glycocoll were added; the mixture was left to stand for 2 hours at laboratory temperature before being dialyzed for 24 hours against a 0.3M NaCl solution containing $CaCl_2$ (1 mM) and $MnCl_2$ (1 mM). After dialysis and centrifugation, 1 ml glycerol was added and the preparation was stored in a freezer at −20° C.

EXAMPLE 2

Preparation of a lectin-antibody conjugate using p-benzoquinone

A-by antibody activation:

The antibodies and the Con.A were dialyzed against a 0.15M NaCl solution.

To the antibody solution (4 mg in 0.7 ml), 70 µl of 1M phosphate buffer pH 6 and 100 µl p-benzoquinone (in a 40 mg/ml alcoholic solution) were added successively. Following incubation for 1 hour in the dark, and at ambient temperature, the preparation was filtered on a Sephadex G25 column (0.9×20 cm). The first peak obtained (1.6 ml) contained the activated antibodies. These were then mixed with 6 mg of Con.A (360 µl). 200 µl 1M dicarbonate-carbonate buffer pH 9 were added to the mixture. This was maintained at 4° C. for 48 hours. The reaction was stopped by the addition of 100 µl 2M glycocoll. Two hours later, the mixture was dialyzed against a 0.30M NaCl solution containing $CaCl_2$ (1 mM) and $MnCl_2$ (1 mM) and then centrifuged. An equal volume of glycerol was then added. The preparation was stored at −20° C.

B-by activation of lectin Con.A

Con.A, previously dialyzed against a 0.15M NaCl solution was activated in the following manner:100 µl of p-benzoquinone (40 mg per ml of ethanol) were added to the Con.A solution (5.4 mg in 0.6 ml) containing 0.1M phosphate buffer pH 6, and 0.1M methyl-α-D-mannoside. One hour later, the preparation was filtered through Sephadex G25. The first peak was recovered (1.7 ml) and mixed with 0.6 ml of antibodies (3.5 mg) and 230 µl of 1M bicarbonate-carbonate buffer pH 9. After standing for 48 hours at 4° C., the mixture was dialyzed, centrifuged and then mixed with an equal volume of glycerol. The preparation was stored at −20° C.

EXAMPLE 3

Preparation of a lectin-antigen conjugate

The same procedure was used as that described in example 1, using sheep immunoglobins instead of sheep anti-rabbit Ig antibodies.

In this example, the following ingredients were used in the proportions given below.

| Con. A 28.8 mg/ml | Sheep Ig 4.4 mg/ml | Phosphate buffer pH 6.8 1 M | 1 M methyl-α-D-mannoside | Glutaraldehyde 1% |
|---|---|---|---|---|
| 174 µl = 5 mg | 568 µl = 2.5 mg | 90 µl | 90 µl | 20 µl |

The solution obtained was stored at −20° C.

EXAMPLE 4

Assay of antibodies and antigens

A. determination of antibodies

The following system was selected as the experimental model:determination of antibodies present in rabbit sera immunized with bovine serumalbumin.

The wells in a polystyrene plate were coated with bovine serum-albumin. After adsorption, the wells were washed with a phosphate buffer solution containing "Tween" 20 (1°/oo), referred to hereinafter as PBS-Tween. Rabbit immunserum was diluted from 1/40,000 to 1/10,240,000 in PBS containing gelatine (0.5%) and Tween 20 (1°/oo). 200 µl of each dilution was placed in the wells. A control was effected using serum from a non-immunized rabbit instead of the immunserum. After incubation (2 hours at 37° C.) and washing 5 times with PBS-Tween, all the wells received 200 µl of a solution of the conjugate of sheep anti-rabbit Ig antibodies Con.A (5 µg/ml) prepared as in example 1 above. The diluent consisted of 0.3M NaCl containing 1 mM $CaCl_2$, 1 mM $MnCl_2$, Tween (0.5%), gelatine (0.5%) and methyl-α-D-mannoside. After 2 hours at 37° C., the wells were emptied and washed with PBS-Tween. 200 µl of a peroxydase solution (10 µg/ml) in 0.15M NaCl containing 0.5% "Tween 20", 1 mM $CaCl_2$ and 1 mM $MnCl_2$, were placed in the wells. After incubation at 37° C. for 3 hours, the wells were again washed with PBS-Tween and then filled with 200 µl of the peroxidase substrate ($H_2O_2$+o-phenylene diamine). 15 minutes later the enzymatic reaction was stopped by the addition of 50 µl 3N HCl. The optical density was measured at 492 nm.

| Dilution | Mean optical density (OD) |
|---|---|
| 1/40,000 | 2,325 |
| 1/80,000 | 1,477 |
| 1/160,000 | 1,019 |
| 1/320,000 | 662 |
| 1/640,000 | 341 |
| 1/1,280,000 | 181 |
| 1/2,560,000 | 120 |
| 1/5,120,000 | 72 |
| 1/10,240,000 | 23 |
| Control: normal rabbit serum | |
| 1/40,000 | 160 |

B-determinations of antigens

A procedure similar to that described hereinabove was used to assay human IgE.

This procedure comprises the fiollowing steps:
Adsorption of anti-IgE antibodies on a polystyrene plate.
Incubation (2 hours) of the serum of the patient to be assayed; diluent:PBS containing Tween 20 and 1% bovinealbumin.
Incubation (2 hours) with anti-IgE antibodies coupled with Con.A (5 µg/ml); diluent:PBS containing 0.1M methyl-α-D-mannoside.
Incubation (3 hours) with peroxidase (10 µg/ml) diluted in 0.15M NaCl containing 1 mM $CaCl_2$ and 1 mM $MnCl_2$.
Enzymatic reaction, 30 minutes
Measurement of optical density at 492 nm.

By following the reaction diagram, it was possible to determine human IgE between 1 and 500 I.U./ml.

EXAMPLE 5

Assay of antigens by erythroadsorption

This assay is effected in the same manner as has been described in detail with respect to immunoenzymatic determination in example 4 except that, for the third incubation (incubation with the enzyme) the enzyme is replaced by a suspension of 0.1% non-sensitized sheep red blood cells. After incubation for 2 hours, the final dilution of the immunoserum or the antigen giving an erythroadsorption which is still visible is noted. The spcificity of this assay is proved by non-erythroadsorption when the immunoserum is replaced by a normal serum, and by inhibition and adsorption in the presence of methyl-α-D-mannoside. The results obtained with the determination of rabbit immunserum bovine anti-bovine albumin are given below.

TABLE 1

| Rabbit anti-bovine albumin immunserum | Erythroadsorption of erythrocytes | Erythroadsorption of erythrocytes in the presence of 0.1 M methyl-α-D-mannoside |
| --- | --- | --- |
| 1/160,000 | +++ | — |
| 1/320,000 | +++ | — |
| 1/640,000 | +++ | — |
| 1/1,280,000 | +++ | — |
| 1/2,560,000 | ++ | — |
| 1/5,120,000 | + | — |
| Normal serum 1/10,000 | — | — |

EXAMPLE 6

Assay of α-foetoprotein in human sera by erythroadsorption

By using a process similar to the one of example 5, the α-foetoprotein was assayed in human sera.

This process comprises the following steps:
adsorption of anti-α-foetoprotein antibodies on a polystyrene microplate having wells with a section in "V" or "U" form.
incubation (2 hours) of the human serum to be assayed (diluent:PBS+"Tween" (1°/$_{oo}$)+bovine albumine (1%))
incubation (2 hours) with anti-α-foetoprotein antibodies coupled with Con.A (diluent:PBS containing 0.1M of methyl-α-D-mannoside) and "Tween" (1°/$_{oo}$)
incubation (2 hours) with red blood cells of sheep, determination of erythroadsorption (visual).

These tests were carried out, on one hand with normal human sera (No. 1,2 and 3) having been previously submitted to an absorption of sheep red blood cells in order to remove the possible anti-red blood cell antibodies present in the sera, and on the other hand with samples of the same sera which were not submitted to such an absorption.

This absorption was effected according to the process previously defined in the case of the thermolabile antigens.

As reference, a standard serum (cord serum) having a α-foetoprotein concentration of 66 µg/ml was used.

The obtained results are in table 2.

Sera No. 1,2 and 3 are normal sera, i.e. sera which contain no or very few E-foetoprotein. The data of table 2, show that the invention process may give wrongly positive reactions if care is not taken to previously absorb the sera with sheep red blood cells, if red blood cells are used as labellers in the invention process.

TABLE 2

| Dilution of standard serum (serum of cord) | Erythroadsorption without previos absorption of serum by the sheep red blood cells | Erythroadsorption with previous absorption of serum by the sheep red blood cells | | | |
| --- | --- | --- | --- | --- | --- |
| 1/500 | ++++ | ++++ | | | |
| 1/1,500 | ++++ | ++++ | | | |
| 1/4,500 | +++ | +++ | | | |
| 1/13,500 | — | — | | | |
| 1/40,500 | — | — | | | |
| Dilution of human serum to be tested | serum N° 1 | serum N° 2 | serum N° 3 | serrum N° 1 | serrum N° 2 | serrum N° 3 |
| 1/3 | ++++ | ++++ | ++++ | ± | — | — |
| 1/9 | +++ | ++++ | ++++ | — | — | — |
| 1/27 | ++ | ++ | ++++ | — | — | — |
| 1/81 | ± | — | ++++ | — | — | — |
| 1/243 | ± | — | +++ | — | — | — |

EXAMPLE 7

Immunocytochemical detection of immunoglobulines of immunocytes by means of the lectin-antibody conjugate Suspensions of lymphocytes obtained from various lymphoid organs were cytocentrifuged on a slide, or cellular smears were taken of these suspensions. The cellular preparations were then fixed, followed by incubation in PBS containing 10 µg/ml sheep antimice immunoglobulins antibodies coupled with Concanavaline A and methyl-α-D-mannoside 0.1M. After incubation for one hour, the cellular preparations were washed with PBS and then incubated with PBS containing horseradish peroxidase or glucose oxidase at a concentration of 100 µg/ml. After 2 hours incubation at laboratory temperature, the slides were washed and the enzyme associated with cells was revealed by a histochemical stain specific to the enzyme used as label.

EXAMPLE 8

This example illustrates the use of a substance labelled with a fluorochrome, viz., glucose oxidase labelled with fluorescein isothiocyanate.

(a) To label glucose oxidase with fluorescein, the procedure is as follows:

3 mg glucose oxidase is dissolved in 140 µl of 0.15M NaCl. After stirring there is added 48 µl of fluorescein isothiocyanate (10 mg/ml) solution in 1M bicarbonate pH 9.5. The solution is left to stand for 4 hours at laboratory temperature. The product obtained is flowed through a column packed with Ultragel Ac-A-202 (trade name registered by the Industrie Biologique Francaise-Pharmaindustrie) previously washed with 0.15M NaCl. Elution is effected with the same NaCl solution and the fractions containing the glucose oxidase labelled with fluorescein are recovered.

(b) The procedure for antibody and antigen assay is identical to that previously described. The presence of the antibody-Con A conjugate is revealed by incubation with glucose oxidase that has been rendered fluorescent. Measurement of fluorescence is effected either in the supernatent after incubation or in the eluate after treatment of the solid phase with a dissociating reagent, such as urea, sodium dodecylsulphate acid or alkaline buffers, concentrated solutions of strong acid (6N HCl) or strong base (6N NaOH), and other similar products, or by the specific sugar of lectin (example 1M methyl-α-D-mannoside).

Results of actual experiments conducted with glucose oxidase labelled with fluorescein are given in table 3 below.

TABLE 3

| Dilution of glucose oxidase labelled with fluorescein | Fluorescence (units of fluorescence) | | |
|---|---|---|---|
| | in the starting solution | in the supernatent after incubation | in the wells* |
| 1/100 | 155 UF | 150 | 2.9 |
| 1/500 | 35 | 27 | 2.6 |
| 1/1,000 | 19 | 12 | 2.4 |

*measured after dissociation with methyl-α-D-mannoside (1 M) of the bond between the Con. A and the labelled glucose oxidase.

EXAMPLE 9

This example illustrates the use of a substance labelled with a radioactive isotope, viz., glucose oxidase labelled with $^{125}$I.

The technique used in example 7 for fluorescence is applicable in this system, but the measurement of radioactivity in the wells, on the solid phase, replaces fluorescence measurement.

Results of actual trials effected with $^{125}$I labelled glucose oxidase are given in table 4 below:

TABLE 4

| Dilution of $^{125}$I labelled glucose oxidase | Radioactivity measured for each saucer after elution with 6N NaOH | | |
|---|---|---|---|
| | Ac Con. A* 1/100 | Ac Con. A* 1/1,000 | Ac Con. A* 0 |
| 1/10 | 45,000 cpm | 7,500 cpm | 350 |
| 1/30 | 30,000 cpm | 5,700 cpm | 210 |
| 1/90 | 6,500 cpm | 3,000 cpm | — |
| 1/270 | 2,400 cpm | 550 cpm | 90 |
| 1/810 | 1,000 cpm | 200 cpm | |

*Ac Con. A = Antibody coupled by glutaraldehyde with Concanavalin A.

EXAMPLE 10

This example illustrates the technique of reading by hemolysis.

After specific erythroadsorption, the red blood cells that have not reacted with the reagent (antibody-lectin) decant and fall to the bottom of the wells. The decanted red blood cells are then carefully drawn up with a pipette.

The red blood cells bound to the reagent (antibody-lectin) remain in the wells. Distilled water, or any other liquid enabling lysis of the red blood cells is then added. Lysis occurs immediately. Reading is effected by absorption at 403 nm of the released haemoglobin.

The results of actual tests are given in table 5 below:

TABLE 5

| Dilution of the antibody* lectin conjugate** | $DO_{403\ nm}$ |
|---|---|
| 1/500*** | 488 |
| 1/1000 | 365 |
| 1/2000 | 336 |
| 1/4000 | 272 |
| 1/8000 | 217 |
| 1/16,000 | 133 |
| 1/32,000 | 88 |
| Control without conjugate | 83 |

*the antibody being rabbit antiimmunoglobuline
**the lectin being Concanavalin A
***for the dilution at 1/500, the concentration was 2 µg/ml antibody and 4 µg/ml Concanavalin A.

EXAMPLE 11

Assay of a rabbit anti-BSA immunserum by erythroadsorption using a conjugate antibody-Con.A This assay was effected by using a process similar to the ones disclosed in above examples 5 and 6.

This process comprises the following steps:
adsorption of bovine serum albumine (BSA) on polystyrene microplates with V or U wells,
incubation with rabbit immunserum;
incubation with the antibody-Con.A conjugate obtained according to the process of example 1, the antibody being sheep anti-rabbit Ig antibody.
incubation with sheep red blood cells,
determination of the erythroadsorption.

The determination of the erythroadsorption was effected by three different manners:
(1) visually
(2) after hemolysis of red blood cells by measuring of optical density at 405 nm,
(3) after hemolysis and enzymatic reaction using ortho-phenylene-diamine as substrate by measuring the optical density at 492 nm.

The obtained results are in table 6.

The specificity of such an assay using the conjugate of the invention was demonstrated by total inhibition by pre-incubating the anti-BSA immunserum with an excess of BSA.

TABLE 6

| Dilution of rabbit anti-bovine albumine immunserum | visual reading | Determination of erythroadsorption | |
|---|---|---|---|
| | | hemolysis and reading of OD* at 405 nm | hemolysis and enzymatic reaction and OD at 492 nm |
| 1/10,000 | ++++ | 0.177 | 0.986 |
| 1/20,000 | ++++ | 0.180 | 0.981 |
| 1/40,000 | ++++ | 0.167 | 0.847 |
| 1/80,000 | ++++ | 0.153 | 0.834 |
| 1/160,000 | +++ | 0.141 | 0.762 |
| 1/320,000 | ++ | 0.098 | 0.555 |
| 1/640,000 | + | 0.078 | 0.453 |
| 1/1,280,000 | ± | 0.042 | 0.278 |
| 1/2,560,000 | − | 0.004 | 0.086 |
| 1/5,120,000 | − | 0.000 | 0.044 |
| normal rabbit serum 1/10,000 | − | 0.000 | 0.007 |

*OD: optical density.

EXAMPLE 12

Assay by erythroadsorption using antibody—WGA conjugate.

A antibody WGA conjugate obtained by the procedure disclosed in example 1 was used and the assay was carried out erythroadsorption of the following antibodies or antigens using substantially the procedures disclosed in hereinabove examples 5 and 6:

Total human IgE
Anti-graminaceae pollen specific human IgE
Anti-CMV antibodies (cytomegalovirus)
Antihydatidose antibodies
Anticandida albicans antibodies
Antiaspergillus fumigatus antibodies The obtained data were compared with the ones obtained by conventional immunological techniques, such as the quantitative radioimmunoassay for total human IgE and anti-graminaceae pollen specific human IgE, the passive hemagglutination for anihydatidose antibodies and anti-CMV antibodies and electrosyneresis for anticandida albicans antibodies and antiaspergillus fumigatus antibodies.

In each case a good correlation between the erythroadsorption and the conventional techniques was found with a statistically significant correlation coefficient.

We claim:

1. A process for the immunological assay of a biological substance, which comprises the steps of:
   (1) immobilizing a substance having a binding affinity for said biological substance to be determined;
   (2) incubating said substance with a medium containing said biological substance to be determined;
   (3) incubating, after washing, the resulting reaction medium with a conjugate of a lectin-specific ligand in solution in an aqueous medium containing an excess of a sugar specific to lectin, said ligand being capable of reacting specifically with said substance having an affinity to the biological substance to be determined or with said biological substance itself;
   (4) washing the resulting reaction medium and incubating it with a labeller bearing glycosidic fractions capable of reacting with said lectin; and
   (5) revealing said labeller by suitable means.

2. Process according to claim 1, wherein said labeller is chosen from the group consisting of an enzyme, a substance containing a radioactive isotope, a fluorochrome, and a particulate substance capable of reacting with said lectin.

3. Process according to claim 2, wherein the particulate substance consists of red blood cells.

4. Process according to claim 3, wherein in order to reveal the red blood cells used as labeller the unreacted red blood cells used as labellers are removed, the red blood cells bound to the lectin-ligand conjugate are lysed, and the substances released by the red blood cells are determined.

5. Process according to claim 4, wherein the lysis is effected with distilled water.

6. Process according to claim 1 or 2, wherein the liquid medium containing the biological substance to be assayed is a serum and wherein the serum is previously absorbed by red blood cells.

7. Process according to claim 6, wherein said serum is absorbed by red blood cells according to the procedure which comprises the following steps:
   (1) decomplementing of the serum by heating at about 56° C. for about 30 minutes;
   (2) adding an excess of red blood cells of sheep to said serum, in order to obtain a concentration in red blood cells of 10%;
   (3) leaving said serum at ambient temperature for about one hour under smooth stirring; and
   (4) centrifuging in order to recover the purified serum and above the bottom of red blood cells.

8. Process according to claim 6, wherein the serum is absorbed by red blood cells treated with a tanning agent, such as glutaraldehyde.

* * * * *